US006248353B1

(12) United States Patent
Singh

(10) Patent No.: US 6,248,353 B1
(45) Date of Patent: Jun. 19, 2001

(54) RECONSTITUTION OF PURIFIED MEMBRANE PROTEINS INTO PREFORMED LIPOSOMES

(75) Inventor: Pratap Singh, Wilmington, DE (US)

(73) Assignee: Dade Behring Inc., Deerfield, IL (US)

( * ) Notice: Subject to any disclaimer, the term of this patent is extended or adjusted under 35 U.S.C. 154(b) by 0 days.

(21) Appl. No.: 09/459,137

(22) Filed: Dec. 10, 1999

(51) Int. Cl.[7] .......................... A61K 35/14; A61K 38/00; A61K 9/127; C07K 1/00; C07K 14/00

(52) U.S. Cl. ..................... 424/450; 424/943; 530/350; 530/381; 436/829

(58) Field of Search ............................... 424/450; 1/94.3; 436/829; 530/381, 350

(56) References Cited

U.S. PATENT DOCUMENTS

| | | | |
|---|---|---|---|
| 5,248,590 | 9/1993 | Rutner et al. | 435/5 |
| 5,314,695 | 5/1994 | Brown | 424/450 |
| 5,599,909 | 2/1997 | Fickenscher et al. | 530/402 |
| 5,625,036 | 4/1997 | Hawkins et al. | 530/381 |
| 5,631,019 | 5/1997 | Marx | 424/450 |
| 5,651,982 | 7/1997 | Marx | 424/450 |
| 5,698,677 | 12/1997 | Eibl et al. | 530/381 |

FOREIGN PATENT DOCUMENTS

| | | |
|---|---|---|
| 0 359 201 | 9/1989 | (EP) . |
| 0 464 533 A1 | 6/1991 | (EP) . |
| WO 92/08479 | 5/1992 | (EP) . |
| 0 566 333 A1 | 4/1993 | (EP) . |
| 603 671 A2 | 12/1993 | (EP) . |
| 0 585 987 A1 | 7/1998 | (EP) . |

OTHER PUBLICATIONS

R. Colman, et al., Chapter 1, Overview of Hemostatis, *Plasma Coagulation Factors*, pp. 3–18.
H. Karges, et al., Activity of Coagulation and Fibrinolysis Parameters in Animals, *Drug Res. 44(1)*, 6. 793–797 (1997).
R. Palmer, et al., Cold–Induced Contact Surface Activation of the Prothrombin Time in Whole Blood, *Blood*, vol. 59, p. 38–42, 1982.
A. Darszon, et al., Incorporatin of Membrane Proteins Into Large Single Bilayer Vesicles, *J. Cell Biology*, The Rockefeller University Press, vol. 81, May 1979, pp. 446–452.
J. L. Rigaud, et al., Incorporation of Bacteriorhodopsin Into Large Unilamellar Liposomes By Reverse Phase Evaporation, *Biochemical and Biophysical Research Communications*, vol. 111, No. 2., Mar. 16, 1983, pp. 373–382.
G. Eytan, et al., Incorporation of Biologically Active Proteins Into Liposomes, *FEBS Letters*, vol. 57, No. 2, Sep. 1975, pp. 121–125.
A. Saxena, et al., Isolation and Reconstitution of the Membrane–bound Form of Dopamine β–Hydroxylase, *The Journal of Biological Chemistry*, vol. 258, No. 7, Apr. 10, 1983, pp. 4147–4152.

A. Scotto, et al., Reconstitution of Membrane Proteins. Spontaneous Association of Integral Membrane Proteins with Preformed Unilamellar Lipid Bilayers, *Biochemistry*, 1985, 24, 4066–4075.
A. Scotto, et al., Reconstitution of Membrane Proteins: Catalysis by Cholesterol of Insertion of Integral Membrane Proteins into Preformed Lipid Bilayers, *Biochemistry 1986*, 25, 1555–1561.
Strategies for Membrane Proteins Reconstitution Into Liposomes, pp. 72–87.
A. Darszon, et al., Reassembly of protein–lipid complexes into large bilayer vesicles: Perspectives for membrane reconstitution, *Proc. Natl. Acad. Sci. USA*, vol. 77, No. 1, pp. 239–243, Jan. 1980.
T. Thomas, et al., Purification of Membrane Proteins, *Methods in Enzymology*, vol. 182, pp. 499–520 (1990).
J. Lawson, et al., Extrinsic Pathway Proteolytic Activity, pp. 177–193 (incomplete).
L. Mimms, et al., Phospholipid Vesicle Formation and Transmembrane Protein Incorporation Using Octyl Gluoside, *Biochemistry*, 1981, 20, 833–840.
F. Cornelius, et al., Liposomes in Reconstitutin of Ion–Pumps, *Handbook of Non–medical Applications of Liposomes*, vol. II, pp. 219–243.
Coagulation Cascade, *Clinical Neuro.*, Aug. 97.
Product Sheet For Liquid Rabbit Brain Cephalin with Plasma Activator, *BaxterDiagnostics, Inc.*, Jan. 1992.
H. Talsma, et al., Liposomes as Drug Delivery Systems, Part II: Characterization, *Pharmaceutical Technology*, Nov., 1992, pp. 52–58 (only even pages).
H. Talsma, et al., Liposomes as Drug Delivery Systems, Part III: Stabilization, *Pharmaceutical Technology*, Jan., 1993.
Product Sheet For Dade Actin FSL Activated PTT Reagent, *Dade International, Inc.*, Feb. 1996.
Product Sheet For Dade Thromboplastin IS, *Dade International, Inc.*, Aug. 1995.
Product Sheet For Dade Determination of INR (International Normalized Ratio), *Dade International Inc.*, Jan. 1996.

(List continued on next page.)

Primary Examiner—Karen Cochrane Carlson
Assistant Examiner—Holly Schnizer
(74) Attorney, Agent, or Firm—Cara Lowen; Linda Buckley

(57) ABSTRACT

The present application relates to a method of making liposomes having membrane proteins incorporated therein, the method comprising: providing the membrane protein in solution; providing a solution of preformed liposomes; and incubating the mixture. Prior to the step of providing a solution of preformed liposomes, the liposomes are formed by combining a mixture of phospholipids with a solution of at least one type of unsaturated fatty acid. The methods of the present invention further relate to the method of making a reagent comprising tissue factor reconstituted into preformed liposomes. The method of the present invention for making a tissue factor reagent comprises: providing tissue factor in solution; providing a solution of preformed liposomes comprising a mixture of phospholipids and at least one type of unsaturated fatty acid; and incubating the mixture.

22 Claims, No Drawings-

OTHER PUBLICATIONS

Product Sheet For Dade Innovin, *Dade International*. Inc. Feb. 1996.

R. Bach, et al., Factor VII Binding to Tissue Factor in Reconstituted Phospholipid Vesicles: Induction of Cooperativity by Phosphatidylserine, *Biochemistry 1986, 25*, 4007–4020.

J. Neuteboom, et al., Use of Synthetic Phopholipids in An Aptt Reagent For Monitoring Treatment With Heparin, Abstract, Thromb Haemostas, 65 (6) 645–1417 (1991) Jun. 5, 1991.

H. Penefsky, et al., Extraction of Water–Soluble Enzymes and Proteins from Membranes, pp. 205–219.

M. Jain, et al., The Spontaneous Incorporation of Proteins Into Preformed Bilayers, *Biochemica et Biphysica Acsta* 906 (1987) 33–68.

G. Eytan, et al., Incorporation of Biologically Active Proteins Into Liposomes, *FEBS Letters*, vol. 57, No. 2, Sep. 1975, pp. 121–125.

L. Lorand, Introduction to Clotting and Lysis in Blood Plasma, Methods in Enzymology, vol. XLV, Proteolytic Enzymes, Part B, *Academic Press*, 1976, pp. 31–37.

G. Henry, et al., Methods to Study Membrane Protein Structure in Solution, *Methods in Enzymology*, vol. 239, 1994, pp. 515–541.

An Ultra–Sensitive Prothrombin Time Reagent, Dade Innovin, Dade Behring Website, Mar. 9, 1997.

Colman, R.W., et al., "Overview of Hemostasis" in "Hemostasis And Thrombosis: Basic Principles and Clinical Practice". W. Salzman, Hirsh, J. Marder and W. Colman (editors) p. 3; Lippincott Williams and Wilkins Publishers, Hagerstown, Md. (1994).

Rigaud, J.L., et al., "II Strategies for membrane proteins reconstitution into liposomes:" in Chapter 5: "Liposomes as tools for the reconstitution of biological systems" in "Liposomes as Tools in Basic Research and Industry," edited by Jean R. Philippot and Francis Schuber. CRC press Boca Raton, FL (1995).

J. H. Lawson, et al., "Extrinsic Pathway Proteolytic Activity," *Methods in Enzymology* 222: 177–1195 (1993).

Cornelius, F., et al., "Liposomes in reconstitution of ion–pumps", in "Handbook of Nonmedical Applications of Liposomes: Theory and Basic Sciences, vol. 1". Danilo D. Lasic and Yechezkel Bareholz (editors) p. 219; CRC press, Boca Raton, FL. (1996).

H.F. Penefsky and A. Tzagoloff, "Extraction of Water–soluble enzymes and proteins from membranes," *Methods in Enzymology* 22: 204–230 (1971).

RECONSTITUTION OF PURIFIED MEMBRANE PROTEINS INTO PREFORMED LIPOSOMES

FIELD OF THE INVENTION

The present invention relates to methods of incorporating membrane proteins into preformed liposomes. It further relates to methods of making a prothrombin time (PT) reagent using purified, reconstituted natural or recombinant human tissue factor (rTF). More particularly, the invention relates to the reconstitution of tissue factor (TF) into phospholipid liposomes to produce a tissue factor-based PT reagent.

BACKGROUND OF THE INVENTION

Membrane proteins are critical for cellular function and include receptors, ion pumps, electron transport proteins, signal transducers and regulators of the intracellular environment. The isolation and reconstitution of these proteins into membranes has been well studied and is well documented.

Liposomes are a general category of vesicles which comprise one or more lipid bilayers surrounding an aqueous space. Liposomes include unilamellar vesicles composed of a single membrane or lipid bilayer, and multilamellar vesicles (MLVs) composed of many concentric membranes (or lipid bilayers). Liposomes are commonly prepared from phospholipids. Due to unique characteristics of these vesicles, liposomes have been widely used as a model membrane for investigating the properties of biomembranes and for studying the functions of membrane proteins.

There are essentially four presently known mechanisms for incorporating, i.e., reconstituting, proteins into liposomes. See Rigaud, J- L., et al., "Liposomes as Tools for the Reconstitution of Biological Systems," p. 71–88, in Liposomes as Tools in Basic Research and Industry, ed. Philippot, J. R. and Schuber, F., CRC Press, Boca Raton, Fla. (1995). One method involves the use of an organic solvent. However, such procedures often result in the denaturation of the proteins. A second method uses mechanical means to produce large and small unilamellar vesicles from MLVs by swelling of the dry phospholipid films in excess buffer. Such mechanical means include sonication of MLVs, forcing multilamellar lipid vesicles through a French press, or cycles of freeze-thawing or dehydration-rehydration. Drawbacks with sonication include variability and inactivation of certain proteins by sonication as well as production of small liposomes. A third process involves the direct incorporation of proteins into preformed small unilamellar liposomes, also termed spontaneous incorporation. Such methods are usually catalyzed by low cholate or lysolecithin concentrations. Problems with these methods include the wide size distribution of the proteoliposomes, heterogeneous distribution of the protein among the liposomes and presence of the non-phospholipid impurities, required for an effective protein incorporation, that would affect performance of those liposomes. The fourth and most often used method of incorporating proteins into liposomes involves the use of detergents. In such a method, the proteins and phospholipids are cosolubilized in a detergent to form micelles. The detergent is then removed, resulting in the spontaneous formation of bilayer vesicles with the protein incorporated therein. The detergent is incorporated into liposome as well as the protein and thus, these methods require removal of the detergent by methods such as dialysis, gel exclusion chromatography or adsorption on hydrophobic resins. The methods that use detergent are very slow because the detergent removal must be as complete as possible and also because a phase change that takes place during this process slows detergent removal even further. The detergent is also difficult to remove completely. Another disadvantage is that one cannot control the orientation of protein incorporated into the liposomes by using the detergent methods.

Liposomes have several properties which make them useful in various applications. The most important of these characteristics are the uniform controllable size and the surface characteristics which can control the biological fate of the liposomes. These properties make liposomes preferred carriers for drug delivery systems and the basis for reagents for assays. For example, liposomes containing tissue factor have been used as reagents for prothrombin time (PT) assays for testing coagulation of blood. In these cases, the phospholipid constituent of the liposomes is used as a substitute for platelet phospholipids, which are essential for normal hemostasis in vivo. For example, Dade Behring Inc. presently produces INNOVIN® for use in PT determinations and prothrombin time-based assays. This product is prepared from purified human tissue factor produced in *E. coli* combined with synthetic phospholipids (thromboplastin), calcium, buffers and stabilizers.

Coagulation of blood occurs by two pathways, the intrinsic pathway and the extrinsic pathway. In the intrinsic (endogenous or foreign contact dependent) pathway the chain of events leading to coagulation is set in motion merely by exposure of plasma to nonendothelial surfaces, such as glass in vitro or collagen fibers in basement membranes in vivo. In contrast, the extrinsic (exogenous or tissue-dependent) pathway is initiated when, as a result of outside injury to the vessel wall, tissue juice becomes mixed with components of the blood plasma.

It has been observed that the tissues of vertebrates, when added to citrated plasma and recalcified, will profoundly accelerate clotting time. This tissue constituent which has been observed to activate the coagulation protease cascades by the extrinsic pathway is commonly referred to as thromboplastin or tissue factor (TF).

Tissue factor is a membrane-associated glycoprotein which functions by forming a complex with blood coagulation factors VII and VIIa. The complexing of these factors greatly enhances the proteolytic activity of factors VII and VIIa. Functional activity of tissue factor has an absolute dependence on the presence of phospholipids. Bach, Ronald R., *Initiation of Coagulation by Tissue Factor*, CRC Critical Reviews in Biochemistry 1988; 23 (4): pp. 339–368. The factor VII/VIIa/tissue factor complex activates a series of specific enzymes that comprise the extrinsic and common pathways of the coagulation cascades ultimately leading to the formation of thrombin, fibrin, platelet activation, and finally clot formation. Nemerson, Yale, *Tissue Factor and Hemostasis*, Blood 1988; 71:pp. 1–8.

Screening tests for coagulation disorders are designed to detect a significant abnormality in one or more of the clotting factors and to localize this abnormality to various steps in the coagulation pathway. Commonly used screening tests for this purpose include the activated partial thromboplastin time (APTT) and the prothrombin time (PT). Diagnostic tests such as the PT test, utilize this series of enzymatic events in vitro under controlled conditions to diagnose disfunctions in the blood coagulation system of patients. In the PT test, the time it takes for clot formation to occur, is the Prothrombin time or "PT value".

The PT test is performed by adding tissue thromboplastin with calcium to plasma. This initiates clotting by activating Factor VII which in turn activates Factor X which in the presence of Factor V, lead to the conversion of prothrombin to thrombin. The thrombin which is so produced converts fibrinogen to fibrin. PT therefore bypasses the intrinsic clotting pathway and is normal in patients with deficiencies of Factors XII, XI, IX and VIII. PT is abnormal in patients with deficiencies of Factors VII, X, V, prothrombin or fibrinogen. Tissue thromboplastin is a phospholipid extract (from rabbit brain or lung and human brain or placenta) to which calcium has been added. It is usually provided in a lyophilized form and must be reconstituted with distilled water.

The prothrombin time (PT) test is the most commonly performed assay in the coagulation laboratory.

PT assay reagents are particularly useful in rapid screening tests to detect single or combined deficiencies of the extrinsic coagulation system indicative of hereditary and acquired coagulation disorders, liver disease or vitamin K deficiency. PT assay reagents are also used in monitoring tests for oral anticoagulant therapy and assays for specific coagulation factors.

Tissue factor is one example of a membrane protein. Membrane proteins (e.g. receptors) are composed of one or more transmembrane domains together with intracellular and extracellular domains. The activity of such proteins is frequently measured following integration of the purified protein into an artificial membrane. Tissue factor is a receptor for factor VII of the blood coagulation system and is composed of apoprotein and lipids (Pitlick, F. A. and Nemerson, Y., Binding of the protein component of tissue factor to phospholipids. Biochemistry (1970) 9 (26): 5105-13). The apoprotein is a glycosylated polypeptide of 263 amino acids. Close to the carboxy-terminal end, it possesses a hydrophobic sequence of 23 amino acids by which it is anchored in the membrane. The intracellular moiety is composed of 21 amino acids (Fisher, K. L. et al. Cloning and expression of human tissue factor cDNA. Thromb. Research (1987) 48: 89–99); Morrissey, J. H. et al. Molecular cloning of the cDNA for the tissue factor, the cellular receptor for the initiation of the coagulation protease cascade. Cell (1987) 50: 29–35). In vivo, tissue factor is present as an integral membrane protein of cells which are not in direct contact with the blood. Its physiological function as a cell-surface receptor comprises binding and activating plasma coagulation factor VII upon coming into contact with blood or plasma. This complex possesses serine protease activity and is able to activate factors IX and X and thereby trigger coagulation.

Fickenscher, K. and Zender, N. F. (U.S. Pat. No. 5,599,909) describe a process of relipidization of isolated tissue factor that does not use detergents and is achieved by acidifying and/or heating a protein/lipid mixture. This process involves mixing protein and phospholipids at sufficiently low pH values. In this process, the phospholipids are not dissolved with the aid of a detergent, but instead, are emulsified in an aqueous solution. Appropriate pH ranges are taught to be between pH 1 and 5, preferably between pH 2 to 4, particularly preferably at a pH of about 3. The relipidization can be carried out using a membrane protein which is dissolved or one which is bound to an affinity column (e.g., an immunoadsorption column containing a polyclonal or monoclonal antibody). An aqueous emulsion of phospholipids is initially mixed with buffer at acid pH. Purified membrane protein is subsequently added to this acidic emulsion, and mixed. After an incubation time between 1 and 10 minutes, the pH of the mixture can be adjusted to the desired value immediately after mixing the protein sample to achieve homogeneity. Subjecting these proteins to low pH may cause denaturation of the protein and affect removal of acid-labile groups, such as certain glycosidic linkages. Loss of such groups from proteins may affect specific binding sites present in these proteins.

Fickenscher and Zender (U.S. Pat. No. 5,599,909) also teach a second method for integrating membrane proteins into a lipid membrane. This method uses the process of heating a protein in the presence of phospholipids. As in the process involving acidification, the lipids are not dissolved with the aid of detergents but rather by heating the mixture at 80 to 95° C. for 1 to 10 minutes. Subsequently, the mixture is cooled to room temperature within between 1 and 10 minutes and buffer is subsequently added. Following relipidization, the membrane protein is incorporated into a lipid membrane in active form. Suitable additives can be added and the liposomes subjected to further processing. If tissue factor apoprotein is relipidized using one of the processes according to the invention, its use as a therapeutic agent or diagnostic agent becomes possible. In the second case, the relipidized tissue factor can be processed to produce a reagent for determining the prothrombin time for the purposes of examining blood coagulation in plasma. However, heating at these temperatures may result in irreversible protein unfolding, denaturation and precipitation.

As mentioned above, INNOVIN® is one example of a commercial product in which a membrane protein is incorporated into liposomes. Because INNOVIN® is manufactured from recombinant human tissue factor and synthetic phospholipid, it does not contain any other clotting factors, such as prothrombin, Factor VIII and Factor X. Furthermore, INNOVIN® is from a pure source, unlike other commercially available PT reagents that contain crude tissue factor extracted from natural sources such as rabbit brain, rabbit brain/lung mixtures, human placenta or ox brain. Each of these sources has limitations. For example, rabbit brain thromboplastin shows seasonal variability, lot-to-lot variability and is dependent on reliable raw material sources. Human tissue factor may be a source of HIV or other human viral diseases and is also dependent on reliable sources. Ox brain gives normal PT values that are much longer than those which use tissue factor from other common sources. Longer PT values lead to less throughput in the clinical laboratory. Additionally, these longer times may reflect differences in the ability of ox tissue factor to bind human factor VII. Moreover, crude tissue factor preparations from natural sources contain other coagulation factors as contaminants. Contamination with coagulation factors results in coagulation factor assay curves that are less sensitive to coagulation factor-deficient plasmas. Therefore, it is desirable to use a source of tissue factor, which does not suffer from these drawbacks and has improved lot-to-lot variability to create a more reproducible PT reagent.

INNOVIN® is highly sensitive to factor deficiencies and oral anti-coagulant-treated plasma samples. The sensitivity of INNOVIN® is similar to the WHO human brain reference thromboplastin. INNOVIN® is also insensitive to therapeutic levels of heparin. This combination of properties makes INNOVIN® very useful for monitoring oral anticoagulation therapy. Because INNOVIN® is so sensitive, it allows differentiation of abnormal plasmas, even in mildly pathological ranges. This tissue factor reagent and the methods for preparing the same are described by Hawkins P. L., et al. (Patent No. WO 93/07492 and U.S. Pat. No. 5,625,036), both incorporated herein by reference. The reagent is generally made by combining purified tissue factor, in a detergent such as octylglucoside, with natural or synthetic phospholipids, also solubilized in a detergent solution. The detergents are then removed by diafiltration or dialysis to form lipid micelles that contain tissue factor. It would be useful to have a method of preparing a tissue factor reagent, such as INNOVIN®, without the need to use dialysis or diafiltration to remove the detergent.

SUMMARY OF THE INVENTION

The present invention relates to methods for reconstituting purified membrane proteins into preformed liposomes, in the presence of at least one type of fatty acid. In one preferred embodiment, the present invention relates to such methods that do not use detergent.

The present application relates to a method of making liposomes having membrane proteins incorporated therein, the method comprising: providing the membrane protein in solution; providing a solution of preformed liposomes; and incubating the mixture under physiological conditions of temperature and pH. Prior to the step of providing a solution of preformed liposomes, the liposomes are formed by combining a mixture of phospholipids with a solution of at least one type of unsaturated fatty acid. The fatty acid comprises an unsaturated fatty acid having from about 16 to about 20 carbon atoms. Preferably, the fatty acid comprises oleic acid. In preferred methods, the oleic acid is present in an amount ranging from about 10 to about 35 weight percent, preferably from about 15 to about 30 weight percent, and most preferably about 16 weight percent.

In the method of the present invention, the membrane protein is solubilized. Preferably the protein is solubilized in a salt solution. In a preferred embodiment the protein is solubilized in 50 mM Hepes-150 mM NaCl, pH 7.40 containing 40–50% trifluoroethanol, 60% alcohol or 20–40% DMSO or by exchanging with 50 mM Hepes-0.5 M NaCl, pH 7.40. Preferably, the protein is solubilized by exchanging a detergent solution of the protein with a buffer containing salt such as 50 mM Hepes-0.5 M NaCl, pH 7.40.

The preformed liposomes for use in the methods of the present invention comprise either natural or synthetic phospholipids. The mixture of phospholipids comprises a mixture of phospholipids containing saturated or unsaturated mono or disubstituted fatty acids and a combination thereof. These phospholipids are selected from dioleoylphosphatidylcholine, dioleoylphosphatidylserine, dioleoylphosphatidylethanolamine, dioleoylphosphatidylglycerol, dioleoylphosphatidic acid, palmitoyloleoylphosphatidylcholine, palmitoyloleoylphosphatidylserine, palmitoyloleoylphosphatidylethanolamine, palmitoyloleoylphophatidylglycerol, palmitoyloleoylphosphatidic acid, palmitelaidoyloleoylphosphatidylcholine, palmitelaidoyloleoylphosphatidylserine, palmitelaidoyloleoylphosphatidylethanolamine, palmitelaidoyloleoylphosphatidylglycerol, palmitelaidoyloleoylphosphatidic acid, myristoleoyloleoylphosphatidylcholine, myristoleoyloleoylphosphatidylserine, myristoleoyloleoylphosphatidylethanoamine, myristoleoyloleoylphosphatidylglycerol, myristoleoyloleoylphosphatidic acid, dilinoleoylphosphatidylcholine, dilinoleoylphosphatidylserine, dilinoleoylphosphatidylethanolamine, dilinoleoylphosphatidylglycerol, dilinoleoylphosphatidic acid, palmiticlinoleoylphosphatidylcholine, palmiticlinoleoylphosphatidylserine, palmiticlinoleoylphosphatidylethanolamine, palmiticlinoleoylphosphatidylglycerol, palmiticlinoleoylphosphatidic acid. These phospholipids may also be the monoacylated derivatives of phosphatidylcholine (lysophophatidylidylcholine), phosphatidylserine (lysophosphatidylserine), phosphatidylethanolamine (lysophosphatidylethanolamine), phophatidylglycerol (lysophosphatidylglycerol) and phosphatidic acid (lysophosphatidic acid). The monoacyl chain in these lysophosphatidyl derivatives may be palimtoyl, oleoyl, palmitoleoyl, linoleoyl myristoyl or myristoleoyl. Preferably, the mixture of phospholipids comprises dioleoylphosphatidylcholine and dioleoylphosphatidylserine in a ratio of from about 4 to about 1. In preferred methods, the dioleoylphosphatidylcholine and dioleoylphosphatidylserine are in a ratio of from about 7 to about 3. In preferred methods the phospholipids are synthetic.

As mentioned above, the method of the present invention involves the step of incubating the mixture of membrane protein and liposomes between 25° and 45° C. but preferably at about 37° C. Preferably the mixture is heated from about 30 minutes to at least an hour, preferably for about an hour.

The mixture is then diluted with the appropriate buffer, for example, Hepes-based buffer, pH 7.4 containing salt, BSA, calcium chloride, dextran, glycine and preservative.

The methods of the present invention further relate to the method of making a reagent comprising tissue factor reconstituted into preformed liposomes. The method of the present invention for making a tissue factor reagent comprises: providing tissue factor in solution; providing a solution of preformed liposomes comprising a mixture of phospholipids and at least one type of unsaturated fatty acid; and incubating the mixture under the physiological temperature of 37° C. The mixture of phospholipids preferably comprises a mixture of phospholipids selected from dioleoylphosphatidylcholine, dioleoylphosphatidylserine dioleoylphosphatidylethanolamine, dioleoylphosphatidylglycerol, dioleoylphosphatidic acid and the fatty acid preferably comprises oleic acid.

The methods of the present invention provide a method to combine membrane proteins, e.g., tissue factor, with preformed liposomes which is more efficient and reproducible than presently used methods. The present invention also relates to a PT reagent which has a high degree of sensitivity and reproducibility for determining PT values. The PT reagent of the present invention is sensitive to the overall function of the coagulation system. The methods of the present invention provide a PT reagent with a well-defined clotting time for normal plasma samples and which prolongs the clotting times of abnormal plasma samples. The methods of the present invention also provide a PT reagent with minimal lot-to-lot variability and enhanced stability and optical clarity.

DETAILED DESCRIPTION OF THE INVENTION

The present invention relates to methods of reconstituting purified membrane proteins into preformed liposomes. The present methods enable such reconstitution without the use of detergent, as required in presently heretofore known methods. The term "detergent" refers to amphipathic compounds, for example long-chain hydrocarbon, terminated at one end by a polar group, often charged. These compounds include molecules whose charged polar group is highly soluble in water whereas the hydrocarbon does not readily enter the aqueous environment. Detergents, as used herein, include those without any charge, e.g., n-octyl-β-D-glucopyranose (octylgluside), anionic detergents, which carry a negative charge, e.g., dodecyl sulfate, and cationic detergents, which carry a positive charge, e.g., hexadecyltrimethylammoniumbromide.

In one embodiment of the present invention, the protein that is incorporated into the liposomes is a purified tissue factor. The protein is active as demonstrated by showing clotting activity which is comparable to that of tissue factor in liposomes obtained by previously known methods, e.g., by using detergent.

As discussed briefly above, previous known methods of reconstituting TF into phospholipid mixture include heating a mixture of protein and phospholipids at low pH (U.S. Pat. No. 5,599,909). However, the disadvantage of this method is that low pH heating may cause aggregation and irreversible denaturation of the liposomes and irreversible denaturation of the proteins. Another popular method involves the use and removal of detergent. Disadvantages of this method however, include the fact that it is a very slow process and phase change that takes place during this process slows detergent removal even more. The detergent may be incorporated into liposome, in addition to the protein, which may lead to leaky and fragile liposomes. The detergent is difficult to remove completely and finally, one cannot control the orientation of protein incorporated into the liposomes.

The methods of the present invention enable the reconstitution of purified membrane proteins into preformed liposomes without the need to use detergent for the step of reconstitution.

As described briefly above, the present methods of making liposomes having membrane proteins incorporated therein, comprise the steps of providing the membrane protein in solution; providing a solution of preformed liposomes; and incubating the mixture under physiological conditions. The preformed liposomes are made by a method comprising combining a mixture of phospholipids with a solution of at least one type of unsaturated fatty acid.

The phospholipids which are used to form the preformed liposomes in the methods of the present invention comprise either natural or synthetic phospholipids. The phospholipids are selected from phospholipids containing saturated or unsaturated mono or disubstituted fatty acids and combinations thereof. These phospholipids are dioleoylphosphatidylcholine, dioleoylphosphatidylserine, dioleoylphosphatidylethanolamine, dioleoylphosphatidylglycerol, dioleoylphosphatidic acid, palmitoyloleoylphosphatidylcholine, palmitoyloleoylphosphatidylserine, palmitoyloleoylphosphatidylethanolamine, palmitoyloleoylphophatidylglycerol, palmitoyloleoylphosphatidic acid, palmitelaidoyloleoylphosphatidylcholine, palmitelaidoyloleoylphosphatidylserine, palmitelaidoyloleoylphosphatidylethanolamine, palmitelaidoyloleoylphosphatidylglycerol, palmitelaidoyloleoylphosphatidic acid, myristoleoyloleoylphosphatidylcholine, myristoleoyloleoylphosphatidylserine, myristoleoyloleoylphosphatidylethanoamine, myristoleoyloleoylphosphatidylglycerol, myristoleoyloleoylphosphatidic acid, dilinoleoylphosphatidylcholine, dilinoleoylphosphatidylserine, dilinoleoylphosphatidylethanolamine, dilinoleoylphosphatidylglycerol, dilinoleoylphosphatidic acid, palmiticlinoleoylphosphatidylcholine, palmiticlinoleoylphosphatidylserine, palmiticlinoleoylphosphatidylethanolamine, palmiticlinoleoylphosphatidylglycerol, palmiticlinoleoylphosphatidic acid These phospholipids may also be the monoacylated derivatives of phosphatidylcholine (lysophophatidylidylcholine), phosphatidylserine (lysophosphatidylserine), phosphatidylethanolamine (lysophosphatidylethanolamine), phophatidylglycerol (lysophosphatidylglycerol) and phosphatidic acid (lysophosphatidic acid). The monoacyl chain in these lysophosphatidyl derivatives may be palimtoyl, oleoyl, palmitoleoyl, linoleoyl myristoyl or myristoleoyl. Preferably, the mixture of phospholipids comprises dioleoylphosphatidylcholine and dioleoylphosphatidylserine in a ratio of from about 5 to about 1. In preferred methods, the dioleoylphosphatidylcholine and dioleoylphosphatidylserine are in a ratio of from about 7 to about 3. In preferred methods the phospholipids are synthetic. Synthetic phospholipids are readily available commercially from various sources, such as AVANTI Polar Lipids (Albaster, Ala.); Sigma Chemical Company (St. Louis, Mo.).

Naturally occurring phospholipids used in the PT reagent containing recombinant TF include natural phosphatidyl serine (PS) in the range from about 25 to 35% of total phospholipid with the most preferred at about 30% and natural phosphatidyl choline (PC) in the range from about 65 to 75% of total phospholipid with the most preferred at about 70%. The phosphatidylcholine used is neutral in charge, while the phosphatidylserine is negatively charged. In the preferred embodiment the lipid mixture has at least one component with a net negative charge. In other embodiments of this invention it is possible to use combinations of other lipids. A preferred source of the natural PS is from bovine brain and a preferred source of the natural PC is from egg yolk.

Synthetic phospholipids may also be used with the present invention and are preferred. These synthetic compounds may be varied and may have variations in their fatty acid side chains not found in naturally occurring phospholipids. The side chain variations that result in PT reagent improvement are listed above. Preferred compounds have unsaturated fatty acid side chains with C14, C16, C18 or C20 chains length in either or both the PS or PC. Preferred compositions include but are not limited to those that have dioleoyl (18:1)-PS; palmitoyl (16:0)-oleoyl (18:1)-PS, dimyristoyl (14:0)-PS, dipalmitoleoyl (16:1)-PC, dipalmitoyl (16:0)-PC, dioleoyl (18:1)-PC, palmitoyl (16:0)-oleoyl (18:1)-PC, and myristoyl (14:0)-oleoyl (18:1)-PC as constituents.

Optimal activity of the PT reagent is achieved when the tissue factor: synthetic phospholipid ratios are about 1:2,000 to 1:20,000 with the preferred ratio being about 1:10,000. This leads to a final concentration of about 50–300 M of total phospholipids. Thus both the PS:PC and rTF to total phospholipid ratio are essential to achieve and maintain optimal functional activity.

As aforesaid, the methods of the present invention utilize preformed liposomes made from phospholipids and fatty acids. Preferably, the fatty acid comprises an aliphatic unsaturated fatty acid having from about 16 to about 20 carbon atoms. In a preferred embodiment, the fatty acid comprises oleic acid. In preferred methods, the oleic acid is present in an amount ranging from about 15 to about 30 weight percent, preferably about 16 weight percent, to phospholipid.

In the method of the present invention, the membrane protein is solubilized. Preferably, the protein is solubilized in a salt solution. In a preferred embodiment the protein is solubilized in 50 mM Hepes-150 mM NaCl, pH 7.40 containing 40–50% trifluoroethanol or 60% alcohol or by exchanging with 50 mM Hepes-0.5 M NaCl, pH 7.40. Preferably, the pure protein preparation solubilized in presence of a detergent, such as 2% octyl glucoside, is solubilized by exchanging a detergent solution of the protein with a buffer of physiological pH such as 50 mM Hepes containing 0.5 M NaCl at pH 7.40.

The present invention can be used to reconstitute other membrane proteins into preformed liposomes. The proteins useful in the methods of the present invention have a similar structure and biological properties to those of tissue factor. The proteins can be obtained from natural sources or produced synthetically by genetic engineering techniques. Preferably, the proteins are purified to homogeneity to a single uniform specie as monitored by analytical methods such as HPLC, biochemical activity, amino acid composition and electrophoretic pattern. In certain embodiments, the proteins are preferably obtained through recombinant procedures. Such recombinant procedures are known within the art. The use of recombinant protein eliminates the presence of contaminants, such as other proteins which are normally essential for sustaining physiological functions of the specific species.

In preferred embodiments of the present invention, the membrane protein is tissue factor. Preferably the tissue factor that is used in the present methods is a recombinant tissue factor as described by Hawkins, P. L., et al. (U.S. Pat. No. 5,625,136), incorporated herein in its entirety. As discussed above, the use of recombinant tissue factor, as opposed to crude tissue factor from natural sources such as rabbit brain, rabbit brain/lung mixtures, human placenta or ox brain, eliminates problems associated with these sources. The tissue factor was cloned in *E. coli* by procedures similar to that described by Fisher K. L., et al., Cloning and expression of human tissue factor cDNA. Thromb. Res. (1987) 48: 89–99 and Morrissey J. H., et al., Molecular cloning of the cDNA for tissue factor, the cellular receptor for the initiation of the coagulation protease cascade, Cell (1987) 50: 129–135.

The preferred embodiment of the present invention uses a well-defined, purified proteins, e.g., rTF, in combination with liposomes formed from purified, well-defined phospholipids and a fatty acid. Full length as well as truncated recombinant molecules can be used and are prepared pursuant to methods known in the art, e.g., methods of Nemerson and Pabrosky (Spicer E. K., et al. Isolation of cDNA clones coding for human tissue factor: primary structure of the protein and cDNA, Proc. Natl. Acad. Sci. USA (1987) 84: 5148–52; Pabrosky, L., et al. Purification of recombinant human tissue factor. Biochemistry (1989) 28: 8072–77; Fisher K. L., et al. Cloning and expression of human tissue factor cDNA. Thromb. Research (1987) 48: 89–99.); The present invention also encompasses proteins, e.g., rTF, with additions, deletions and substitutions of amino acids that do not diminish the functional activity of the reagent. In a preferred embodiment, the preferred modification of rTF is truncated at or about amino acid residue 243. The preferred concentrations of rTF in the PT reagent are from about 20 to 400 ng/mL and most preferably about 100 to 350 ng/mL. PT reagents made from these raw materials are optically clear without the fine precipitates found in PT reagents based on crude extracts of natural source materials. Since the raw materials are highly purified, chemical analysis gives a meaningful measure of their expected performance. Chemical analysis, in combination with functional assays, provide lot-to-lot consistency, an important clinical consideration.

The PT reagents made from recombinant or natural purified tissue factor in combination with natural phospholipids and synthetic phospholipids with and without variation in side chains offers an improvement in the quality and sensitivity of the PT reagent. Synthetic phospholipids give the advantage of a more reproducible final product and offer the improvement of better controlled functional activity of the PT reagent when the side chains are varied.

The choice of buffers and stabilizers vary widely and can also assist in the stability of the PT reagent. The most preferred embodiments may include calcium ion in the concentration range form about 9 to 15 mM, NaCl in the concentration range from about 0 to 10% with the most preferred range from about 6 to 9%, dextran in the range of about 0 to 5%, a protein such as bovine gamma globulin or bovine serum albumin in the concentration range of about 0–5%; and an appropriate buffer. Buffers, such as N-2-Hydroxyethylpiperazine-N'-2-aminoethane sulfonic acid (HEPES), 3-[N-ris{Hydroxymethyl}methylamino]-2-hydroxy-propane sulfonic acid (TAPSO), 3-(N-Morpholino) propane sulfonic acid (MOPS), N-Tris-(hydroxymethyl) methyl-2-aminoethanesulfonic acid (TES), 3-[N-bis (hydroxyethyl)-amino]2-hydroxypropane sulfonic acid (DIPSO), Piperazine-N,N'-bis (2-hydroxypropane-sulfonic acid) (POPSO), N-Hydroxyethylpiperazine-N'-2-hydroxypropane sulfonic (HEPPSO) and Tris-(hydroxymethyl) aminomethane (TRIS) are preferred in the PT reagent. The most preferred buffers are HEPES or TAPSO in the concentration range of about 20 to 80 mM.

In the preferred embodiment of this invention, the raw material recombinant human tissue factor is grown in vitro in *E. coli*, extracted with a detergent solution and then purified using affinity chromatography methods on immobilized monoclonal antibodies directed against human tissue factor. Bach, Ronald R., *Initiation of Coagulation by Tissue Factor*, CRC Critical Reviews in Biochemistry, 1988; 23 (4):pp. 339–368.

In the methods of the present invention, the solubilized membrane protein is mixed with the preformed liposomes and incubated under physiological conditions. The incubation preferably occurs at or near the transition temperature of the liposomes, e.g., between 25–37° C. In a preferred embodiment which uses a mixture of dioleoylphosphatidylcholine and dioleoylphosphatidylserine (in a ratio of from about 7 to about 3), and oleic acid, the mixture is incubated at about 37° C. The appropriate temperature can be readily selected by one of ordinary skill in the art based upon the teachings contained herein. Preferably the mixture is incubated for from about 30 minutes to at least an hour, preferably for about an hour.

Preferably, the liposomes used have a size ranging from 75 to 150 nm, most preferably about 100 nm. It is preferred that the liposomes have a generally uniform size. This uniformity can be obtained by methods known in the art. Table 1 shows the effect of liposome size on clotting time. The smaller and larger liposomes, e.g., 50 nm and 400 nm, show a longer clotting time. In this table the liposomes were made from 3.15 nM protein /75 $\mu$M phospholipid mixture and sized by extrusion through appropriate size membrane (Avestin, Inc., Ottawa, Canada).

TABLE 1

Effect of size of liposomes on the clotting time

| Size of preformed liposomes | Clotting time (seconds) |
| --- | --- |
| 50 nm | 34.3 |
| 100 nm | 28.7 |
| 400 nm | 54.4 |

The methods of the present invention further relate to the method making reagents for assays comprising proteins useful for those assays reconstituted into preformed liposomes. For example, the reconstituted liposomes can be used for receptor dependent or receptor independent drug delivery, e.g., delivery of receptor independent delivery of growth hormones. These liposomes can also be used as carriers of antigens for antibody production, gene transfer agents, in vaccine manufacture for entrapping viral proteins and to study of enzyme isoforms, including free and membrane bound enzymes with distinctly different physiological functions. The liposomes can also be used to study enzyme catalyzed reactions, especially if the product acts as a very potent inhibitor of the enzyme.

In a preferred embodiment, the methods of the present invention further relate to the method of making a reagent comprising tissue factor reconstituted into preformed liposomes. The method of the present invention for making a tissue factor reagent comprises: providing tissue factor in solution; providing a solution of preformed liposomes; and incubating the mixture under physiological conditions. The step of providing a solution of preformed liposomes further comprises forming the liposomes by combining a mixture of phospholipids with a solution of at least one type of unsaturated fatty acid. The mixture of phospholipids preferably comprises a mixture of phospholipids selected from dioleoylphosphatidylcholine, dioleoylphosphatidylserine, and dioleoylphosphatidylethanolamine. Preferably, the liposomes are formed from a mixture of dioleoylphosphatidylcholine and dioleoylphosphatidylserine and oleic acid. Preferably the dioleoylphosphatidylcholine and dioleoylphosphatidylserine are present in a ratio of 7:3 and the oleic acid is present at 16% (w/w). The liposome prepared from a solution of the phospholipid/oleic acid solution is combined with a solution of tissue factor, solubilized in salt solution, and incubated at 37° C. Preferably the mixture is incubated for about an hour.

If desired, the resulting solution of reconstituted liposomes is then diluted with an appropriate buffer. One example of a useful buffer includes, Hepes-based buffer, pH 7.4, containing salt, BSA, calcium chloride, dextran, glycine and preservative. One of ordinary skill in the art can readily determine an appropriate buffer. Preferred buffers have a pKa in the physiological range.

The methods of the present invention provide a method to combine membrane proteins, e.g., tissue factor, with preformed liposomes which is more efficient and reproducible than presently used methods. The present invention also relates to a PT reagent which has a high degree of sensitivity and reproducibility for determining PT values. The PT reagent of the present invention is sensitive to the overall function of the coagulation system. The methods of the present invention provide a PT reagent with a well-defined clotting time for normal plasma samples and which prolongs the clotting times of abnormal plasma samples. The methods of the present invention also provide a PT reagent with minimal lot-to-lot variability and enhanced stability and optical clarity.

The PT reagents of the present invention are very stable. Once the reconstituted liposomes are formed, they are stable in solution especially if the solution is maintained below the transition temperature of the liposomes. For example, if the transition temperature of the liposomes is about 37° C., then the reconstituted liposome solution is preferably maintained at about 4° C. to about 25° C.

The PT reagent of the present invention can be used in any PT assay for laboratories, emergency room physician office labs and home use. The type of instruments on which these reagents can be used are exemplified by the 700, 800, 1000, 1400 and 1600 series of instruments from Medical Laboratory Automation (MLA), CA540, CA1000 and CA6000 series of instruments from Sysmax, BFA, BCT and BCS series of instruments from Dade Behring, MDA 40 instrument from Organon Technica, ACL100, ACL 1000 and ACL 3000 series of instruments from Instrumentation Laboratories, the BM/Stago STA Series, and Coaguteck from Boehringer Mannheim/Roche. This list of instruments is for information only and is not intended to be exclusive. All other instruments that utilize principles of operation similar to those described here can also be used for these reagents. Preferably the present PT reagent is used in assays performed on the MLA ELECTRA 900C™ or 1000C™ instruments (Medical Laboratory Automation, Inc., Pleasantville, N.Y.). The MLA ELECTRA 900C™ is a computerized coagulation system designed for ease of use and broad testing capability while providing accurate and consistent results. The MLA ELECTRA 900C™ uses photometric detection to perform clotting procedures and chromogenic assays. Cuvettes carrying samples are automatically passed before photometric detectors to determine test results.

The PT reagents of the present invention show normal clotting times when run on MLA ELECTRA 900C™. For example, when used with normal frozen plasma and Coumadine plasma, the PT reagent made according to the methods of the present invention showed clotting times of 12.5 and 39.4 sec, respectively. A control (TFS-62) which comprised a manufactured lot of TF from Dade Behring, prepared by detergent method, showed clotting times of 12.4 and 40.4 sec, respectively, when used with normal frozen plasma and Coumadine plasma.

The following examples are provided to illustrate the present invention and are not intended in any way to limit the scope of the invention.

I. Reconstitution of Purified Tissue Factor into Preformed Liposomes without Added Fatty Acid A. Preparation of Tissue Factor:

Recombinant tissue factor (rTF) present in *E. coli* paste was purified by passage over an immunoaffinity column. The immunoaffinity column (1.6×30 cm), prepared by covalent coupling of anti-rTF monoclonal antibody to activated Agarose, was equilibrated with 20 mM Tris-150 mM NaCl-0.5% octylglucoside, pH 7.40. A 15 mL solution of the rTF (containing 0.66 mg/mL protein in the column equilibration buffer), after initial purification over Q-Sepharose, was loaded on the affinity column. The protein adsorbed on the column was eluted first with 0.1 M acetic acid-150 mM NaCl-0.1% octylglucoside, pH 4.0 and then successively with 0.1 M acetic acid-150 mM NaCl, pH 3.0 buffer containing 0.1 and 2% octylglucoside. Protein fractions eluted in the pH 3.0 buffer were adjusted to pH 7.30 by addition of 0.5 M Tris. These fractions contained 2.3 and 5.9 mg protein, respectively. Both of these protein-containing fractions were found to contain identical proteins, as tested on an SDS-PAGE gel. These fractions were pooled together and mixed with solid octylglucoside to achieve 2% final concentration of the detergent. The eluted protein solution containing the apoprotein rTF (82% recovery) was found to be a single species as tested by SDS-PAGE. Protein concentration was determined by using an extinction coefficient of 1.6 mg mL$^{-1}$ cm$^{-1}$.

Clear protein solution (0.2 mL) in buffer containing 2% octylglucoside, was precipitated with 1.0 mL of cold acetone and the precipitate was suspended in 0.4 mL of trifluoroethanol and diluted with 0.4 mL of 40 mM Hepes-160 mM NaCl, pH 7.40. Clear solutions were obtained when detergent-solubilized solution of the protein were diafiltered in an Amicon ultrafiltration system (YM-10) using 50 mM Hepes-0.5 M NaCl, pH 7.40, 50 mM Hepes, pH 7.40 containing 20% DMSO, 40% DMSO or 60% alcohol.

B. Preparation of Liposomes

A chloroform solution of dioleoylphosphatidylcholine (DOPC; 66 mg; 2.64 mL of 25 mg/mL) and dioleoylphosphatidylserine (DOPS; 28.8 mg; 2.88 mL of 10 mg/mL) was evaporated under a stream of nitrogen. The dry film of the phospholipids was dissolved in 2 mL hexane and organic solvent was removed again under a stream of nitrogen. The dried film of the phopspholipids was suspended in 3.16 mL of 40 mM HEPES-160 mM NaCl, pH 7.40. The phospholipid suspension was sonicated for one minute in a cup horn followed by extrusion through a 100 nm membrane (Avestin Inc., Ottawa, Canada). This process resulted into a transparent milky suspension.

C. Reconstitution:

A solution (20–100 μL) of the apoprotein rTF was incubated with 500 μL of the phospholipid suspension for one hour at 37° C. or overnight at 4° C. For testing on MLA, the protein-phospholipid mixture was diluted in a buffer containing 40 mM Hepes-160 mM NaCl-0.2% BSA-0.2% dextran-4.5% glycine-11 mM CaCl$_2$, pH 7.40.

The final mixture containing liposomes reconstituted with tissue factor were tested on MLA ELECTRA 90OCTM.

II. Reconstitution of Purified Tissue Factor into Preformed Liposomes with Added Fatty Acid A. Preparation of Tissue Factor:

Tissue factor was prepared as described above.

B. Preparation of Liposomes

A chloroform solution of dioleoylphosphatidylcholine (DOPC; 11 mg; 0.55 mL of 20 mg/ mL) and dioleoylphosphatidylserine (DOPS; 4.8 mg; 0.19 mL of 25 mg/mL) was mixed separately with 0, 0.01, 0.02, 0.04, 0.08, 0.16, 0.32 or 0.64 mL of a chloroform solution of oleic acid (20 mg/mL).

The phospholipid mixture containing 0 to 44.7% oleic acid (w/w) was evaporated under a stream of nitrogen. The dry film of the phospholipid mixture was dissolved in 0. 1 mL hexane and organic solvent was removed again under a stream of nitrogen.

The dried film of the phopspholipid mixture was suspended in 0.526 mL of 40 mM HEPES-160 mM NaCl, pH 7.40. The phospholipid suspension was sonicated for one minute in a cup horn followed by extrusion through a 100 nm membrane (Avestin Inc., Ottawa, Canada). This process resulted into a transparent milky suspension.

C. Reconstitution:

A solution (7.5 µL; 0.69 mg/mL) of the apoprotein rTF in 50 mM Hepes-0.5 M NaCl, pH 7.40 was incubated with 100 µL of each of the phospholipid suspension for two hours at 37° C. For testing on MLA 900, the protein-phospholipid mixture was diluted in a buffer containing 40 mM Hepes-160 mM NaCl-0.2% BSA-0.2% dextran-4.5% glycine-11 mM $CaCl_2$, pH 7.40.

The final mixture containing liposomes reconstituted with tissue factor were tested on MLA ELECTRA 900C™.

When the final mixture containing liposomes reconstituted with tissue factor was tested on MLA ELECTRA 900C™, the solution showed clotting times of 12.5 and 39.4 sec., when used with normal frozen plasma and Coumadine plasma, respectively. For this experiment the liposomes contained 58, 25 and 17% (w/w) of DOPC, DOPS and oleic acid respectively. Under identical conditions, a control (TFS-625-manufactured lot of TF prepared by detergent method) showed clotting times of 12.4 and 40.4 sec., respectively.

III. Results

A. NaCl as solubilizing agent:

The best clotting times were achieved using NaCl to solubilize the tissue factor. Table 2 shows that clotting times are higher when tissue factor is solubilized in DMSO, TFE or alcohol. The data shows that organic solvents are less useful than NaCl as a solubilizing agent.

TABLE 2

CLOTTING TIME (SEC) FOR NORMAL HUMAN PLASMA

| Sample | Protein Conc.[a] (nM) | Phospholipid Conc. (µM) | Time (sec) |
|---|---|---|---|
| TFS-625[b] | | 312 | 12.6 |
| RTF/NaCl[c] | 0.54 | 312 | 33.7 |
| RTF/NaCl[d] | 0.54 | 312 | 24.8 |
| RTF/20% DMS[e] | 0.39 | 312 | 51.2 |
| RTF/40% DMSO[e] | 0.35 | 312 | 39.1 |
| RTF/40% TFE[e] | 0.05 | 312 | 146.6 |
| RTF/60% alcohol[e] | 0.11 | 312 | —[f] |

[a]determined from absorption of the solution obtained on exchange of same volume of the recombinant protein solution with the appropriate buffer.
[b]commercial product from Dade Behring.
[c]Solution of the protein in 50 mM Hepes-0.5M NaCl, pH 7.40 incubated with the phospholipid at 4° C.
[d]Solution of the protein In 50 mM Hepes-0.5M NaCl, pH 7.40 incubated with the phospholipid at 37° C.
[e]An appropriate volume of the organic solvent was added to an aqueous buffer mixture containing Hepes and NaCl so that the final buffer concentration was 50 mM Hepes-150 mM NaCl, pH 7.40. This mixed buffer was used to exchange a detergent solution of the protein; the clear protein solution was then incubated with the liposome emulsion in 40 mM Hepes-160 mM NaCl, pH 7.40.
[f]Clotting time greater than the limit of the instrument.

B. Ratio of Oleic Acid

Tables 3a and 3b show that the fastest clotting times are obtained when the phospoholipids used are DOPC and DOPS in a 7:3 ratio and oleic acid is present in a range that includes about 16 to 30 weight percent. The clotting time for a normal patient sample using this set of reagents and instrument is found to be between 13–17 seconds.

TABLE 3a

Effect Of Oleic Acid On Clotting Time Of Human Plasma

| % Oleic Acid in DOPC-DOPS (7:3) | Normal Plasma Clotting time (sec) | Coumadine Clotting time (sec) |
|---|---|---|
| 0.0 | 27.3 | 62.2 |
| 1.25 | 28.1 | 91.8 |
| 2.47 | 23.8 | 69.5 |
| 4.82 | 25.1 | 81.2 |
| 9.2 | 20.3 | 49.4 |
| 16.8 | 15.1 | 43.2 |
| 28.8 | 14.9 | 47.5 |
| 44.7 | 25.3 | 84.5 |

TABLE 3b

Effect Of Oleic Acid On Clotting Time Of Human Plasma

| % Oleic Acid in DOPC:DOPG: DOPS:DOPE (7:1.5: 1.0:1.5) | Normal Plasma Clotting time (sec) | Coumadine Clotting time (sec) |
|---|---|---|
| 0.0 | 21.0 | 78.8 |
| 9.2 | 29.4 | 59.6 |

C. Effect of Liposome Additives on the Clotting Time

Experiments show that increasing the amount of protein does not increase clotting time. Table 4 shows that even when the amount of protein reconstituted doubles, or even quadruples, the clotting time is not significantly changed.

Table 4 also shows that additives, such as cholesterol and palmitic acid increase clotting times.

TABLE 4

Effect of liposome additives on the clotting time

| Liposome additives | Clotting time (sec)[1] | Clotting time (sec)[2] | Clotting time (sec)[3] |
|---|---|---|---|
| DOPC + DOPS + Cholesterol (16%) | 23.0 | | |
| DOPC + DOPS + Palmitic acids (16%) | 29.9 | | |
| DOPC + DOPS + Oleic acid (16%) | 16.4 | 14.1 | |
| DOPC + DOPS + choles. (8%) + Palmitic acid (4%) + oleic acid (4%) | 16.0 | | |
| DOPC + DOPS + oleic acid (16%) (carried out on a different day) | 14.6 | 13.1 | 12.6 |

[1]3.15 nM protein/75 µM Phospholipids
[2]Duplicate (using 6.3 nM protein)
[3]Duplicate (using 12.6 nM protein)

Tables 5 and 6 show that adding other phospholipids comprised of other types of fatty acids can result in increased clotting times.

TABLE 5

| Liposome additive | Clotting time (sec) |
|---|---|
| DOPS + (DOPC + DOPE (10%)) | 28.5 |
| DOPS + (DOPC + DOPE (20%)) | 24.1 |
| DOPS + (DOPC + DOPE (50%)) | 22.0 |

TABLE 6

| Liposome additive | Clotting time (sec) |
|---|---|
| DOPS + (DOPC + MPC[1] (25%)) | 33.5 |
| DOPS + (DOPC + MPC[1] (50%)) | 52.3 |
| DOPS + (DOPC + PPC[2] (25%)) | 39.8 |
| DOPS + (DOPC + PPC[2] (50%)) | 50.8 |

[1]Myristoyl-hydroxy-phosphatidylcholine;
[2]Plamitoyl-hydroxy-phosphatidylcholine All references cited herein are incorporated in their entirety.

The invention has been described in detail with particular references to the preferred embodiments thereof. However, it will be appreciated that modifications and improvements within the spirit and scope of this invention may be made by those skilled in the art upon considering the present disclosure.

We claim:

1. A method of making liposomes having membrane proteins incorporated therein, the method comprising:
    a) providing the membrane protein in solution;
    b) providing a solution of preformed liposomes wherein the liposomes are formed by combining a mixture of phospholipids with a solution of at least one type of unsaturated fatty acid; and
    c) incubating the membrane protein solution of a) with the solution of preformed liposomes of b).

2. The method according to claim 1, wherein the fatty acid comprises an unsaturated fatty acid having from about 16 to about 20 carbon atoms.

3. The method according to claim 2, wherein the fatty acid comprises oleic acid.

4. The method according to claim 1, wherein the step of providing the membrane protein in solution further comprises solubilizing the membrane protein in a salt solution.

5. The method according to claim 1, wherein the mixture of phospholipids comprises dioleoylphosphatidylcholine and dioleoylphosphatidylserine.

6. The method according to claim 5, wherein the dioleoylphosphatidylcholine and dioleoylphosphatidylserine are in a ratio of from about 4 to about 1.

7. The method according to claim 6, wherein the dioleoylphosphatidylcholine and dioleoylphosphatidylserine are in a ratio of from about 7 to about 3.

8. The method according to 1, wherein the phospholipids are synthetic.

9. The method according to claim 1, wherein the solutions are incubated at about 25° C. to about 45° C.

10. The method according to claim 3, wherein the oleic acid is present in an amount ranging from about 15 to about 30 weight percent.

11. The method according to claim 10, wherein the oleic acid is present in an amount about 16 weight percent.

12. A method of making a tissue factor reagent comprising:
    a) providing tissue factor in solution;
    b) providing a solution of preformed liposomes wherein the liposomes are formed by combining a mixture of phospholipids with a solution of at least one type of unsaturated fatty acid; and
    c) incubating the membrane protein solution of a) with the solution of preformed liposomes of b).

13. The method according to claim 12, wherein the fatty acid comprises an unsaturated fatty acid having from about 16 to about 20 carbon atoms.

14. The method according to claim 13, wherein the fatty acid comprises oleic acid.

15. The method according to claim 12, wherein the step of providing the membrane protein in solution further comprises solubilizing the membrane protein in a salt solution.

16. The method according to claim 12, wherein the mixture of phospholipids comprises dioleoylphosphatidylcholine and dioleoylphosphatidylserine.

17. The method according to claim 16, wherein the dioleoylphosphatidylcholine and dioleoylphosphatidylserine are in a ratio of from about 4 to about 1.

18. The method according to claim 17, wherein the dioleoylphosphatidylcholine and dioleoylphosphatidylserine are in a ratio of from about 7 to about 3.

19. The method according to 12, wherein the phospholipids are synthetic.

20. The method according to claim 12, wherein the solutions are incubated at about 25° C. to about 45° C.

21. The method according to claim 14, wherein the oleic acid is present in an amount ranging from about 15 to about 30 weight percent.

22. The method according to claim 21, wherein the oleic acid is present in an amount about 16 weight percent.

* * * * *